US005511560A

United States Patent [19]

Begouen

[11] Patent Number: 5,511,560

[45] Date of Patent: Apr. 30, 1996

[54] METHOD AND APPARATUS FOR SIGNALING PARTURITION IN LARGE FARM ANIMALS

[76] Inventor: Jean-Paul Begouen, Lombost, 03280 Archignat, France

[21] Appl. No.: 307,716

[22] PCT Filed: Apr. 9, 1993

[86] PCT No.: PCT/FR93/00359

§ 371 Date: Oct. 18, 1994

§ 102(e) Date: Oct. 18, 1994

[87] PCT Pub. No.: WO93/20778

PCT Pub. Date: Oct. 28, 1993

[51] Int. Cl.$^{6}$ .......... A61B 5/103

[52] U.S. Cl. .......... 128/775; 128/738

[58] Field of Search .......... 128/738, 774, 128/775, 778; 119/174

[56] References Cited

U.S. PATENT DOCUMENTS

| | | | |
|---|---|---|---|
| 4,217,575 | 8/1980 | Lorette | 128/775 |
| 4,232,686 | 11/1980 | Kamonlade | 128/775 |
| 4,319,583 | 3/1982 | Ingle | 128/775 |
| 4,635,587 | 1/1987 | Leonardo | 128/738 |
| 4,707,685 | 11/1987 | Carrier et al. | 128/775 |
| 5,111,799 | 5/1992 | Serger et al. | 128/738 |

FOREIGN PATENT DOCUMENTS

| | | | |
|---|---|---|---|
| 2382885 | 10/1978 | France . | |
| 2392599 | 12/1978 | France . | |
| 2618051 | 1/1989 | France . | |
| 2224357 | 5/1990 | United Kingdom | 128/775 |

*Primary Examiner*—Max Hindenburg
*Attorney, Agent, or Firm*—Curtis, Morris & Safford; Matthew K. Ryan

[57] ABSTRACT

A device usable in animal husbandry for monitoring calving in large animals by sensing a sustained raised position of the animal's tail. Said device includes a tail position sensor and radio frequency transmitter. The sensor consists of a bearing plate (40), a raised portion (42), straps (44,48) and an arm (50) hinged to the bearing plate so that its position is dependent on that of the animal's tail, as well as a harness. The individual transmitter device comprises an electronic assembly including a power supply battery (62), a magnetically controlled power fuse (64) (ILS micro-circuit breaker), an oscillator and shaping circuit (68) for discontinuously generating, and modulating a radio signal, and a timing means (69) for delaying the power supply and activating the oscillator only after a predetermined time lag. The harness consists of a yoke (13) and two straps (12) each connected both to said sensor (10) and to the lower portion of the yoke via respective resilient linkages.

9 Claims, 2 Drawing Sheets

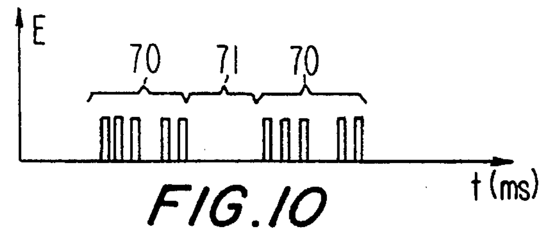
FIG. 10
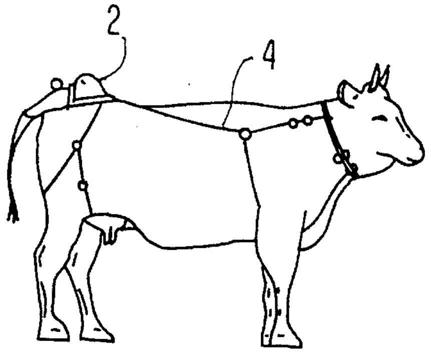
FIG. 1
PRIOR ART
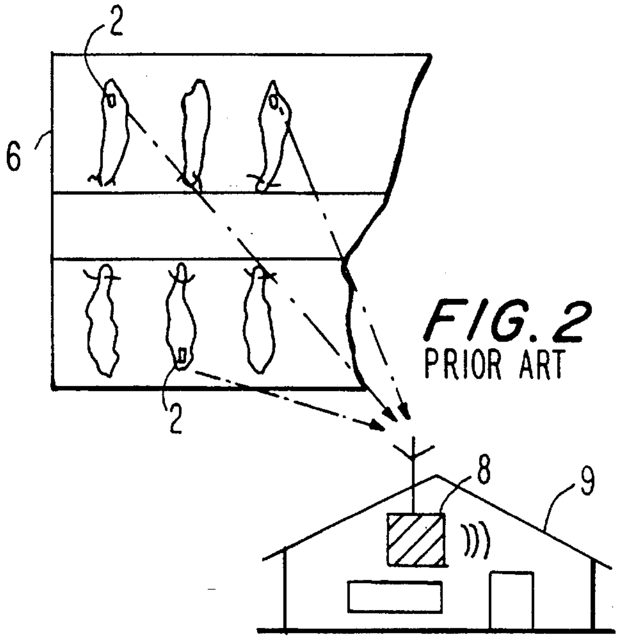
FIG. 2
PRIOR ART
FIG. 3
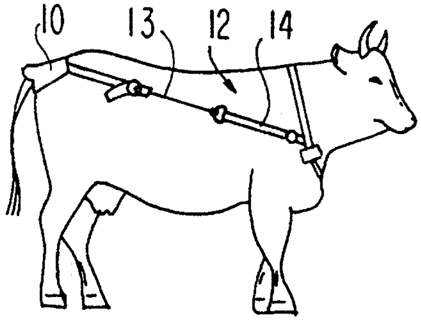
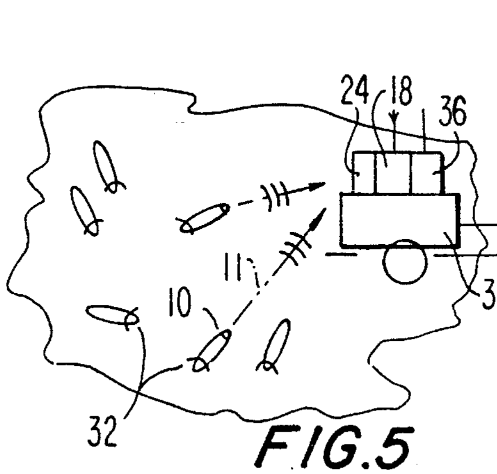
FIG. 5
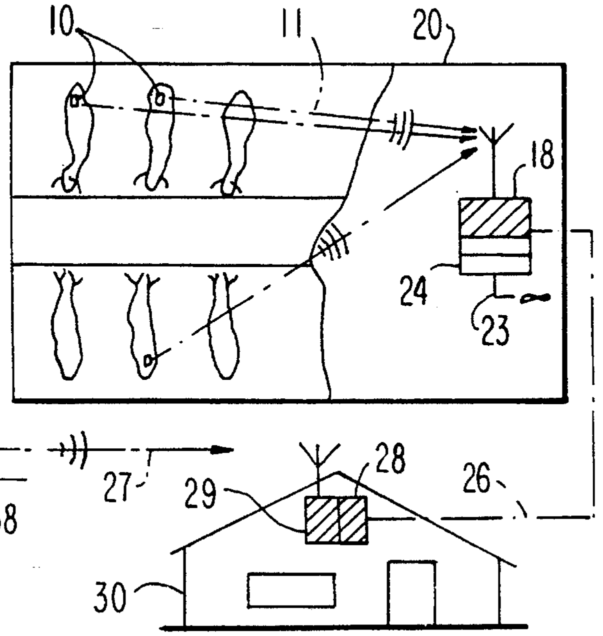
FIG. 4

METHOD AND APPARATUS FOR SIGNALING PARTURITION IN LARGE FARM ANIMALS

FIELD OF THE INVENTION

The present invention relates to the raising of large animals, such as cattle and horses, and its subject matter is improvements in an apparatus for monitoring and signaling the parturition (calving or foaling) of these animals.

BACKGROUND OF THE INVENTION

It is noted that a characteristic phenomenon of the parturition of said large animals consists in holding the tail in raised position for a length of time that has been estimated at two seconds. A prior publication FR-2392599 of the present applicant showed a way, in which this phenomenon has been utilized to alert the cattle or horse raiser to the imminence of parturition, and described a detecting and warning system consisting of a sound alarm mechanism triggered by said phenomenon, wherein the warning is sounded only after an uninterrupted duration of the phenomenon, such duration being measured by an adjustable timer. This mechanism was contained in a box, which can be attached to the rear end of the back of the animal; the distal end of a flexible arm articulated on the box was fastened to the tail and followed its movements.

More recently, improvements have been made in this apparatus, which consist in the replacement of the timing and sounding mechanism with electronic means, each apparatus comprising a microswitch, a radio transmitter and a dry cell power supply; associated with one or more of the transmitters there is a receiver located on the farm where the herd is raised, the herd being free or held in a stable or barn or let out to graze.

This system, although it was satisfactory in operation, had the disadvantage of a relatively high cost because the transmitter in each individual apparatus had to be powerful enough to reach the receiver, particularly in the case of herds in pastures. Furthermore, among large herds, several females can drop young at the same time. This made it necessary, in practice, to provide the herd with a plurality of detectors, without which interest in the monitoring system was lost, also because, even if the herd was not very large, the cost became comparable to that of direct human surveillance.

Another disadvantage was that, since the timing means could be activated by tail movements other than the movement preceding parturition (for example the raising of the tail prior to urination), a large consumption of the electrical energy was required by the electronic timer and this involved very frequent replacement of the batteries. Furthermore, the continual analog radio signal of sufficiently great power to reach the remote receiver also required a great consumption of energy. Other disadvantages connected with the transmission power might result from regulations concerning the use of radio frequencies.

OBJECTS OF THE INVENTION

A first aim of the invention was to lower the cost of the monitoring apparatus taken as a whole, thanks to recent advances in microwave technology, but also to a new method of processing the physical information provided by the phenomenon described above. A second aim of the invention was to render the system more reliable, on the one hand, by adapting it to the physiology of the parturition of the large animals in question and, on the other, by designing the detector so as to protect it almost completely from the hazards (due to shock, rain, barn humidity) encountered in its normal use; another purpose was to reduce its cost of operation in connection with wear and dry-cell replacement.

SUMMARY OF THE INVENTION

Pursuant to the invention, an apparatus intended for the employment of a method of surveillance and signaling of the parturition of large animals, such as bovines and horses, the method being of the kind wherein the physiological phenomenon consisting in the animal holding its tail in a raised position for an uninterrupted period of time longer than a preset period, a phenomenon indicating the imminence of parturition, said method being practiced by means of an apparatus, called an individual apparatus, for detecting said position and emitting radio frequencies, affixed to the posterior part of the back of the animal, and a receiving and warning apparatus located near a human monitor, an apparatus in which, furthermore, a detector is structurally composed of a bearing plate in the shape of a gutter formed by two inclined planes and a substantially parallelepipedal roof ridge, supporting straps, a sub-caudal strap called a tail strap and an arm equipped with a ring for holding the tail of the animal, said arm being articulated on the bearing plate so as to draw a magnetized weight towards said electronic assembly when the tail of the animal assumes the raised position, is characterized in that the individual transmitter apparatus consists of an electronic assembly comprising a power supply dry cell, a magnetically operated power supply circuit breaker (ILS microbreaker), an oscillating and waveshaping circuit for producing and modulating a radio signal in a discontinuous manner, timing means for delaying the application of power and starting the oscillator only after the passage of the preset time period. The result of this arrangement is low consumption of electric energy, namely the consumption of the energy necessary for discontinuous radio transmission when the detector senses parturition.

An important idea of the invention was therefore to assign as many of the functions as possible to a relay station intermediate between the individual detectors and the alarm system, particularly with regard to energy consumption, so as to render the individual detectors as inexpensive as possible, as regards both their manufacture and their power supply.

The invention has several interconnected subject matters for the attainment of the above purposes, such as a new, more ergonomic and simpler configuration of the detection equipment, a method of processing the data delivered by the latter and a particular arrangement of the electronic assembly of the detector.

According to another aspect of the method of the invention, the individual detector emits a radio signal, called an individual or primary signal, which is discontinuous or periodically interrupted, or also "chopped." This discontinuity has the effect, on the one hand, of sparing the batteries, which do not put out power during the periods of interruption and the effect of producing a modulation, which both avoids picking up parasitic signals and permits identification of the signal emitted by one individual detector from the signals from other detectors (in the case of an improved installation for distinguishing the signals).

Pursuant to another aspect of the method, each individual signal is captured by a single receiver, called a "relay station," located within range of said individual detectors, said relay station serving, upon receiving a first individual signal, called the "primary signal," to emit a signal, called the "secondary signal," to the alarm station located near the human monitor.

A result of this manner of proceeding is that the relay station can be a fixed station having a power capacity that enables it to process the data from the primary signals and relay the secondary signal to a location very far away, while the power supply means (batteries) of the individual detectors need to have but a very low energy capacity.

Again, pursuant to the invention, an apparatus for the surveillance and detection of parturition, in which a detector is structurally composed of a gutter-shaped base plate formed by two inclined planes and a substantially parallelepipedal roof ridge, supporting straps, a sub-caudal strap called the tail strap and an articulated arm provided with a ring for holding the tail, said arm being articulated on the base plate, said apparatus being intended for the practice of the method defined above, is characterized by the much greater set-back of the detector towards the tail of the animal and secondarily by the simplicity of the harness composed of two belts each connected to the detector at one end and to the lower middle portion of the collar at the other, each with the interposition of a variable-tension elastic strap.

BRIEF DESCRIPTION OF THE DRAWINGS

The invention will be better understood and details relating thereto will appear in the description that follows of preferred embodiments thereof, in connection with the Figures in the annexed drawings, wherein:

FIG. 1 shows a detector of the prior art mounted on a cow;

FIG. 2 shows diagrammatically the surveillance method of the prior art, embodying a plurality of detectors from the preceding Figure;

FIG. 3 shows the new detector of the invention for comparison with FIG. 1;

FIG. 4 shows diagrammatically the surveillance method employed by the new detector, applied to a herd in a stable;

FIG. 5 shows a variation of the same method applied to a herd in a pasture;

FIG. 10 is a diagram to explain a radio signal used by the apparatus of the invention.

DETAILED DESCRIPTION OF CERTAIN PREFERRED EMBODIMENTS

Figure 7:
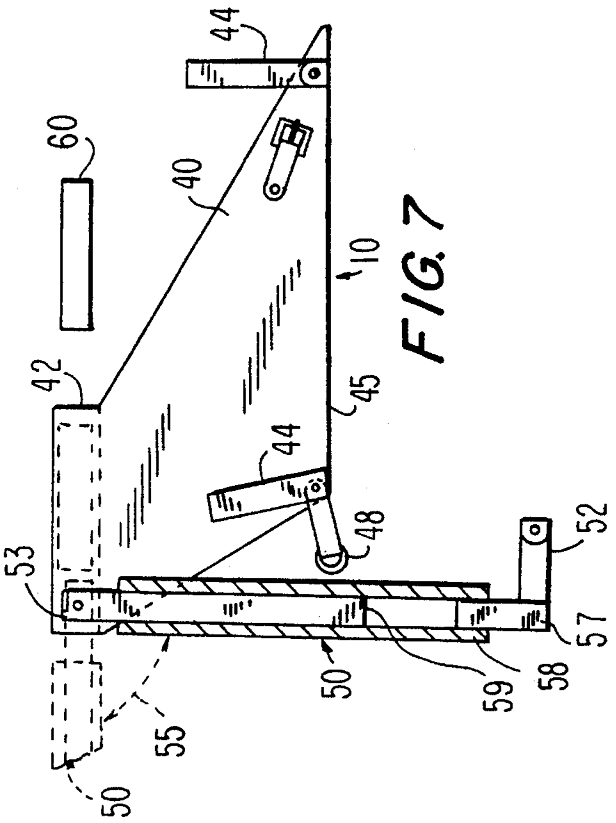
FIG. 7 is a longitudinal section through same.

FIG. 1 shows the very "forward" position of the detector 2 toward the head of the animal, in accordance with the publication cited above, as well as the very complex harness 4.

FIG. 2 shows that the emission from each detector strapped on an animal locked in the stable 6 is received directly by the alarm apparatus 8 located in the remote farmhouse 9; for each detector this requires complex and energy-gluttonous instrumentation.

In FIG. 3, to be compared to FIG. 1, there can be seen the much more "rearward" arrangement of the detector 10 towards the tail of the animal, as well as the simplicity of the harness 12 composed of two straps, such as 14, each connected to the detector 10 at one end and to the lower middle portion of the collar 16 at the other, each with the interposition of an adjustable-tension elastic strap 13.

In FIG. 4, the primary radio signal 11 of each individual detector 10 is captured by the relay station 18 disposed in the barn 20, where the animals are tethered. The relay station is powered from the mains 23, with a stand-by power supply 24; the relay station processes the information received from the detectors and sends via wire 26 an alarm signal, called "secondary," to the alarm station 28 located close to the human monitor, in the farmhouse 30 for example; the wire connection can be one of the wires of the mains.

FIG. 5 proposes an alternative for the case, in which the herd is out in a pasture 32; the relay station 18, disposed on a watering tank 38, for example, is then associated with a large dry cell or battery 34 and with a transmitter 36, the signal 27 of which, emitted after the primary signals have been processed, is received by a radio receiver 29 associated with the alarm apparatus 30.

In FIGS. 6 to 9, the detector 10 has a structure composed of a base plate 40 in the shape of a gutter formed by two inclined planes and a substantially parallelepipedal roof ridge 42, support straps 44, a sub-caudal strap 48 called a tail strap and an arm 50 articulated on the base plate and provided with a ring 52 for holding the tail of the animal. The arm 50 consists of a tube 58 of a pliable and elastic material, into each end of which two hard rods 57 and 59 have been forced, the distal rod 57 serving to hold the ring while the proximal rod 59 serves for the joint and supports the magnet; it will be noted in FIG. 6 that the magnet, in the form of a block 53, is placed on the end face of rod 59 near the joint 54 thereof, so that it is near to the electronic assembly when rod 59 is raised by the tail of the animal (arrows 55, FIG. 7).

The base plate with its top roof ridge is made up of a single piece, formed by heat for example, from plastic material such as polyethylene, so as to be strong and inert and not interfere with the propagation of the radio waves.

Figure 9:
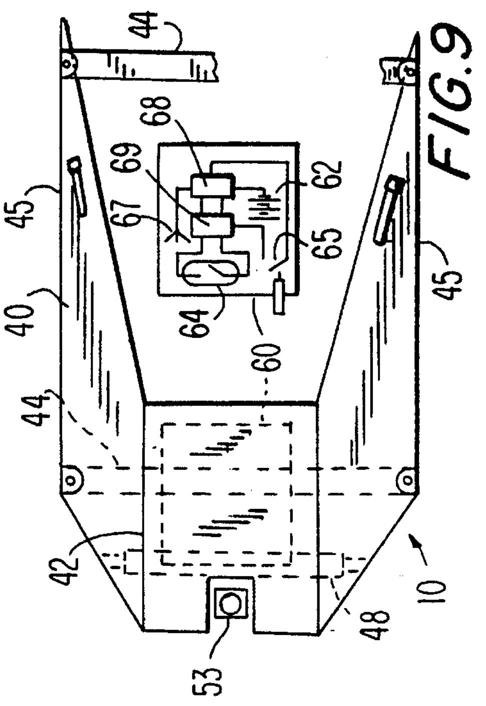
FIG. 9 is a top view thereof.
Figure 6:
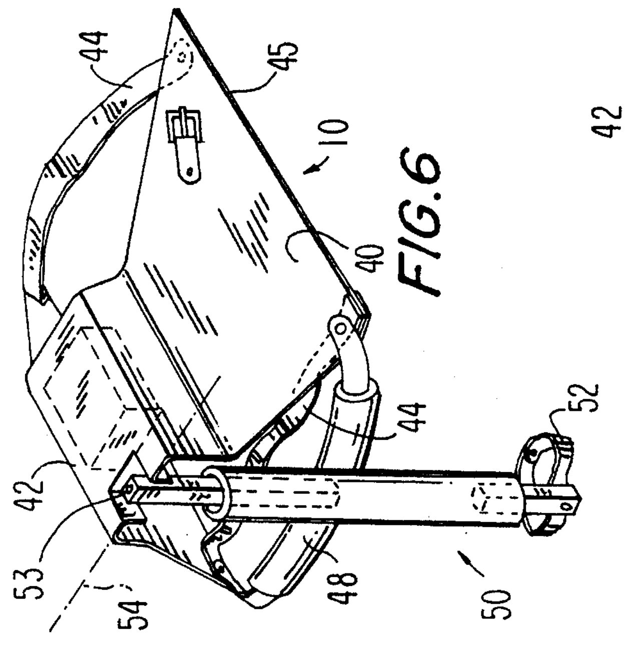
FIG. 6 is a perspective view of the detector of FIG. 2.
Figure 8:
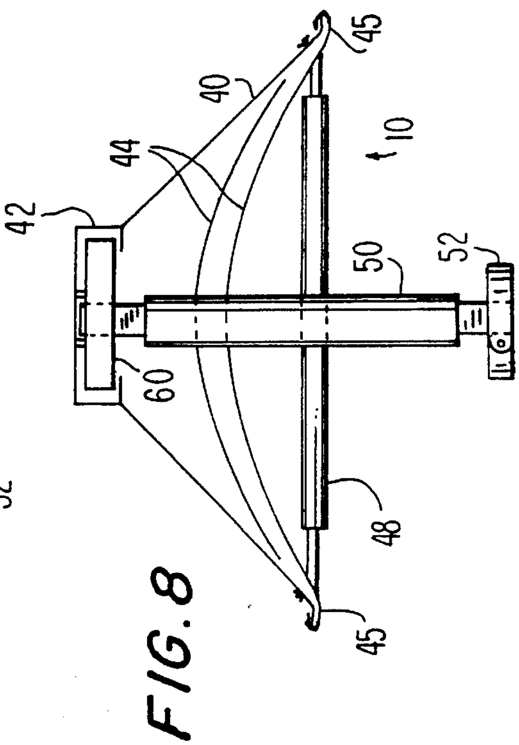
FIG. 8 is an end view thereof.

It will be noted that in these Figures, particularly FIGS. 8 and 9, the roof ridge 42 forms a housing to contain an oblong block 60 containing the individual transmitter apparatus consisting of an electronic assembly including a dry cell 62, a magnetically operated power supply circuit breaker 64 (ILS microswitch), a shaping oscillator 68 for producing and modulating a radio wave in a binary or discontinuous manner according to a code peculiar to the individual detector, timer means 69 to shut off the power and not activate the oscillator until after the passage of the preset time, a moisture-proof switch 65 for testing the operation of the batteries and transmitter and, lastly, an antenna 67; the electronic assembly is enclosed in a water-proof box.

In another embodiment, the electronic assembly, more integrated than the one described above, is potted in a resin (silicone or epoxy, for example) so that, due to the low cost of miniaturized electronics and to the low power consumption needed for the discontinuous radio emission, said assembly can be considered disposable when the dry cell is worn out and can very simply be replaced by the insertion of a new assembly into the compartment in the roof ridge.

In the present embodiment, the timing unit is of the RC (capacitive) type; in another, more integrated form, it could be of the divided-frequency type.

Still, in FIGS. 6 to 9, it is easily seen that the tail strap 48 is situated substantially in the plane formed by the lower edges 45 of the base plate 40 and opposite the joint of the arm, so that, when the apparatus is in place on an animal, the arm normally assumes a position substantially perpendicular to said plane, while the raised position of the tail places it in a position substantially parallel to this plane, so that the magnet is brought close to the electronic assembly in the roof ridge 42; this arrangement of the tail strap results also in a more set-back position of the detector and thus in the possibility of simplifying the harness, and in better ergonomics in relation to the above-mentioned phenomenon and hence greater reliability of the system as a whole.

In FIG. 10, a primary radio signal is emitted in a chopped manner in bursts, which can be regularly spaced to constitute a "simple word," or (in the case of the Figure) irregularly spaced according to a predefined coding to constitute a "coded word" such as the coded words 70; each word, simple or coded and of a duration of a few milliseconds, is separated from the following word by a dead time 71 lasting on the order of one-tenth of a second or more. The result of this arrangement is a saving on the dry cell 62 of block 60, so that the dry cell can have a normal life of several years. It will also be noted that the relay station can also advantageously be provided with indicator lights, indicating which of the individual transmitters (which then must have each a code of its own) has sent the signal.

Although particular forms of the embodiments of the invention have been described and/or represented, it is to be understood that the scope of the invention is not limited to these forms but extends to the general definitions formulated above.

What is claimed is:

1. An apparatus for signaling of the parturition of large animals comprising:
   - a bearing plate in the shape of a gutter formed by two inclined planes and a substantially parallelepipedal roof ridge,
   - supporting straps to maintain the bearing plate affixed to the posterior part of the back of the animal,
   - a subcaudal strap affixed on the bearing plate, situated substantially in the plane formed by the bottom edges of the bearing plate,
   - an arm equipped at its extremity with a ring for holding the tail of the animal and articulated on the bearing plate with a magnet placed close to the joint, the arm normally assuming, when the apparatus is in place on the animal, a position substantially perpendicular to said plane, while the raised position of the tail places the arm in a position substantially parallel to the plane thereby placing the magnet in a position closer to the parallelepipedal roof ridge;
   - an electronic assembly forming a transmitter apparatus and comprising:
     - a power supply dry cell,
     - a magnetically operated power supply circuit breaker (ILS microbreaker),
     - an oscillating and wave-shaping circuit for producing and modulating a radio signal in a discontinuous manner,
     - timing means for delaying the application of power and activating the oscillator only after the passage of the preset time period resulting in low consumption of electric energy, wherein energy is consumed necessary for discontinuous radio transmission when the detector senses parturition in that the tail of the animal has assumed a raised position for an uninterrupted period of time longer than the preset period, so that the imminence of parturition is thereby indicated, and radio frequencies are emitted, and
   - a receiving apparatus located either near a human monitor or a relay station.

2. The apparatus of claim 11, and further including a collar and two belts with each belt being connected to said detector and to the lower part of the collar through an elastic cord.

3. The apparatus of claim 1 wherein said oscillator circuit comprises a shaping circuit to produce and modulate the radio signal in a discontinuous manner.

4. The apparatus of claim 1 wherein the radio signal emitted by an individual detector is a primary signal which has a modulation distinguishable from the signals of the other detectors and wherein said primary signal is a binary signal comprised of alternations of radio emission and absence of emission, the emission absences having a duration longer than $1/10$ of a second.

5. The apparatus of claim 4 wherein each individual signal is captured by a single receiver in the form of a relay station located in range of said individual detectors.

6. The apparatus of claim 5 wherein when said relay station is situated in a pasture its power supply is provided by either a dry cell or a battery.

7. The apparatus of claim 5 wherein when said relay station is disposed in a stabling installation, its power supply is provided by the main voltage with a stand-by battery.

8. The apparatus of claim 7, wherein the relay station is associated with a radio transmitter to provide its radio connection to the alarm apparatus.

9. The apparatus of claim 8 wherein said relay station is connected to an alarm apparatus by a wired connection.

* * * * *

UNITED STATES PATENT AND TRADEMARK OFFICE
CERTIFICATE OF CORRECTION

PATENT NO. : 5,511,560

DATED : April 30, 1996

INVENTOR(S) : Jean-Paul Begouen

It is certified that error appears in the above-identified patent and that said Letters Patent is hereby corrected as shown below:

In column 6, line 20, change "11" to --1--.

Signed and Sealed this

Thirteenth Day of August, 1996

*Attest:*

Bruce Lehman

BRUCE LEHMAN

*Attesting Officer* *Commissioner of Patents and Trademarks*